United States Patent [19]

Feiler

[11] Patent Number: 5,375,603
[45] Date of Patent: Dec. 27, 1994

[54] METHOD OF PERFORMING HEART SURGERY USING THERMOGRAPHIC IMAGING

[76] Inventor: Ernest M. Feiler, 1514 Coral Cove, Champaign, Ill. 61821

[21] Appl. No.: 754,279

[22] Filed: Aug. 30, 1991

Related U.S. Application Data

[63] Continuation of Ser. No. 462,159, Jan. 8, 1990, abandoned.

[51] Int. Cl.$^5$ ............................................. A61B 17/00
[52] U.S. Cl. .................................... 128/664; 128/668; 128/736; 128/898
[58] Field of Search ............. 128/633, 664, 666, 668, 128/691, 736, 897-898

[56] References Cited

U.S. PATENT DOCUMENTS

| | | | |
|---|---|---|---|
| 4,784,150 | 11/1988 | Voorhies et al. | 128/664 |
| 4,995,398 | 2/1991 | Turnidge | 128/668 |

OTHER PUBLICATIONS

Mohr et al., "Thermal Coronary Angiography: A Method for Assessing Graft Patency and Coronary Anatomy in Coronary Bypass Surgery" Ann. Thorac. Surg. (1989) vol. 47, pp. 441–449.

Szabó et al., "Thermography in the Surgical Treatment of Ischemic Heart Disease" Herz 11 (1986) pp. 226–231 (Nr. 4).

Kyo et al., "Thermocardiography in the Ischemic Heart" Heart & Vessels (1985) 1: 244–245.

Robicsek et al., "Experimental Observations of Coronary Blood Flow Using the Thermographic Camera", Coll. Works Cardiopulm Disease, 1979, vol. 22, pp. 57–64.

Shabbo et al., "Thermography in Assessing Coronary Artery Saphenous Graft Patency . . . ", Cardiovascular Research 1982, 16, 158–162.

Robicsek et al. "The Application of Thermography In The Study of Coronary Blood Flow", Surgery, Dec. 1978, 84, 6, 858–864.

Mohr et al., "Thermal Angiography–A New Method of Assessing Coronary Circulation During CABG Surgery" Surgical Forum 38, 1987, pp. 208–210.

Yano et al., "Usefulness of Measurement of Hepatic Arterial Blood Flow During Surgery . . . " Jpn. J. Cancer Chemother., vol. 16, Aug. 1989, pp. 2982–2985.

Harrison's Principles of Internal Medicine, Petersdorf et al. Tenth Edition, 1983, pp. 1334–1343.

Primary Examiner—Angela D. Sykes
Attorney, Agent, or Firm—McDermott, Will & Emery

[57] ABSTRACT

A method of performing heart surgery is disclosed. The method comprises preparing a patient for coronary bypass surgery, assessing blood flow characteristics in the heart region, making decisions on graft locations and the number of grafts based upon the blood flow characteristics and completing the surgery. The method is also useful for surgery on other bodily organs and regions.

26 Claims, 7 Drawing Sheets

METHOD OF PERFORMING HEART SURGERY USING THERMOGRAPHIC IMAGING

This application is a continuation of my copending application Ser. No. 07/462,159, filed Jan. 8, 1990, and now abandoned.

BACKGROUND OF THE INVENTION

The invention of this application relates to methods of performing heart surgery. More particularly, this invention relates to that aspect of coronary artery bypass surgery which is concerned with the choice of arteries to be bypassed.

During coronary artery bypass surgery, the surgeon must make certain decisions about which arteries should be bypassed. Presently, two factors play the primary role in determining the choice of arteries to be bypassed. First, the cardiac catheterization studies before surgery provide information that assists in this decision-making process. After coronary arteries are injected with radiopaque dye, the arteriogram demonstrates which arteries are narrowed and the relative extent of that narrowing. Second, the physician must use his or her experienced judgment about the feel and size of the arteries at the time of surgery. Hard-walled arteries and very small arteries are less likely to be successful graft recipients than soft-walled and larger arteries.

There are short-comings in relying primarily on these two factors. These factors are based on structural considerations rather than upon blood flow and functional considerations. For example, obstructions which are present in primary and secondary branch arteries may not be demonstrated by the arteriogram. This condition can exist in advanced coronary artery disease as well as in diabetics, and also in areas of the heart which have been damaged by heart attacks. Not recognizing these obstructions can lead to inadvertent incomplete revascularization despite technically satisfactory grafts into apparently adequate coronary arteries. Additionally, the presence of small "collateral" arteries can similarly go undetected. Sufficient size and numbers of these small "collateral" arteries can make additional grafts of the large arteries unnecessary. In general, the present determinants are static factors applied to an operative procedure which has dynamic parameters from a medical perspective.

The long-term patency of bypass grafts has been known to depend primarily upon three factors: (1) the head of blood pressure, (2) technically satisfactory grafts and anastomoses, and (3) a good run-off bed.

In coronary bypass grafting, the head of blood pressure always comes from the aorta or one of its main branches, since this is always the best available head of pressure, and, therefore, depends upon the condition of the aorta and its main branches. The adequacy of the grafts and the anastomoses is a result of the skill of the physician. While the skill factor is ultimately determined on a surgeon-by-surgeon basis, it can be generally be assumed that today's highly skilled surgeons in a competitive atmosphere produce generally uniformly good grafts and anastomoses. Because these first two factors largely are predetermined, it can be said that the long-term patency of bypass grafts depends upon the remaining factor, the run-off bed.

It is known that grafts carrying a low flow of blood will very likely clot, and that grafts carrying a high flow of blood will very likely remain patent. Surgeons have been unable adequately to measure the flow requirement of a coronary run-off bed prior to the implantation of a bypass graft. Once a bypass graft is placed and functional, it is at that time possible to estimate the flow requirement of the coronary run-off bed by measuring the flow of blood through the graft with a flow meter. It would be useful to be able to estimate the flow requirement prior to placing a graft, however.

In elective coronary bypass surgery, an attempt is often made to place grafts into all vessels with significant proximal stenoses. Sometimes jump grafts are placed into the same vessel for multiple significant stenoses. In emergency bypasses, sometimes only the most significant stenoses are bypassed, and knowledge of the dynamic flow characteristics in the heart region is incomplete because the patient's condition mandates prompt surgery and the cessation of further studies.

In all of these circumstances, the surgeon must make decisions based on angiographic estimates of restriction of blood flow due to severity of areas of arterial narrowing without knowledge of some other useful and important factors. Some of the factors which the surgeon would not have knowledge of include severity of flow restriction by an area of narrowing, collateral flow of blood from neighboring arteries, shared perfusion beds, or, in some cases, even the status of the remaining arteries. Knowledge of shared perfusion beds is important because placement of competing grafts may endanger the outcome of surgery by jeopardizing the survival of an original graft as well as the competing graft. Also, jump grafts are technically more difficult to perform and are more likely to fail than simple grafts and are, therefore, to be avoided, if possible. Likewise, in some emergency situations, there is insufficient time to perform complete angiography which could indicate the need for further bypass grafts.

In many cases, thermal imaging may help in achieving a thorough revascularization in the shortest time of total cardiopulmonary bypass and with the greatest chance of long-term patency by providing useful and important information that permits the elimination of technical problems with anastomoses and competition of grafts in low flow situations.

The invention disclosed herein comprises a method of performing heart surgery which facilitates decision-making of the surgeon at the operating table by providing non-invasive, on-line information about dynamic variables of concern.

SUMMARY OF THE INVENTION

It is an object of the invention to provide new and useful methods of selecting arteries which are to be bypassed during coronary bypass surgery, as well as the number of arteries to be bypassed. It is a further object to provide new and useful methods of performing heart surgery by using procedures which are based on factors beyond those which are commonly used today.

It is also an object of the invention to provide new and useful methods of performing heart surgery by restricting potentially harmful competitive grafting.

It is another object of the invention to provide surgical techniques which permit the surgeon to consider, at the operating table, which arteries should receive grafts on a dynamic, flow-determined basis rather than relying exclusively on static, structure-related factors. In particular, it is a further object of the invention for the surgeon to be able to judge whether an additional graft is needed in an area where one or more grafts have already been placed, or whether an additional graft would be superfluous or undesirable.

It is yet another object of this invention to provide new and useful methods of peforming heart surgery which can yield improved results over the short term, the long term, or both.

A still further object of the invention is to provide methods of performing heart surgery which employ a means for dynamically estimating blood flow characteristics.

The invention of this application can achieve some of these objects by employing an apparatus that aids in estimating dynamic blood flow in the heart and surrounding areas and visually displays the results of such measurements. One means for dynamically measuring blood flow characteristics is an infra-red sensing device utilized to map surface temperatures of the heart in order to identify areas of inadequate blood flow, areas of distribution of blood flow by individual coronary arteries, and areas adequately supplied with blood flow. This information can be displayed on-line, in color or gray scale with computer enhancement. Further, such information can be saved on a recorder for post-operative evaluation. Some of the objects are achieved by utilizing a means for estimating volumetric blood flow. A means for estimating volumetric blood flow provides information about blood flow on a dynamic and location-specific basis. Once information of the foregoing types is provided to the surgeon, the surgeon can make informed decisions about where to place grafts to improve the likelihood of successful coronary bypass surgery. Also, it will enable the surgeon to make informed decisions in treating surgically some of the results of coronary obstructions, such as acute and chronic aneurysmectomy.

The invention of this application can achieve other of these objects by providing methods of evaluating and preventing potentially harmful competitive grafting of coronary arteries.

Other benefits and advantages of the present invention will become readily apparent to those skilled in the art from the following detailed description of the invention, the drawings and the appended claims.

BRIEF DESCRIPTION OF THE DRAWINGS

In drawings forming a portion of the disclosure of this invention in which cool areas are white and warm areas are black and each area will be identified as supplied by a separate artery.

DETAILED DESCRIPTION OF THE INVENTION

The present invention is directed to methods of performing coronary or heart surgery.

With reference to FIGS. 1–12, after the chest cavity has been opened for surgery on the heart, it is possible to obtain color-coded information about blood flow in and around the heart from a means for dynamically estimating blood flow characteristics. For example, an infra-red sensing device can provide a map or profile of surface temperatures throughout the heart region during surgery. These temperatures can be depicted quite vividly by assigning different colors of the spectrum to predetermined temperature ranges. This graphic depiction of temperature throughout the heart region can be correlated to the blood flow through the heart, the coronary arteries, the grafts, other component and supporting parts, and surrounding areas, giving useful information about the volume of blood flow as well as the flow paths or directionality of the blood flow. By having a constant and dynamic source of information about blood flow in the heart area, the surgeon can make informed decisions about grafting.

The means for dynamically measuring blood flow characteristics described hereinafter is capable of providing a color-graphic or gray scale depiction after the heart temperature is intentionally changed with a perfusing solution. While the heart is arrested, the coronary arteries are perfused with the solution. Exemplary solutions capable of performing this function include cardioplegia solution, vein perfusion solution, and blood solution.

The perfusing solution can be infused into the heart by any of several methods. These include direct infusion into the coronary arteries and infusion into the proximal aorta when it has been distally cross-clamped. Moreover, the heart temperature can be changed by changing the entire body temperature due to circulating cooled or warmed perfusate from a heart-lung machine. The heart may also be cooled externally by instilling a cold solution into the sac around the heart, or by placing a cold, form-adapting device against the surface of the heart.

The temperature or the cooled perfusing solution should have about five degrees Centigrade variance from the temperature of the heart surface prior to the infusion. An infra-red means for dynamically estimating blood flow characteristics can easily measure the temperature of the heart surface, which allows a determination to be made of how cool or warm the perfusing solution should be in order to provide a five degree variance.

Once the coronary arteries are perfused with a solution different in temperature from the surface of the heart by about five degrees Centigrade, areas of temperature change spread out from the coronary artery and its major branches to delineate the perfusion field of each coronary artery. This effect of a spreading temperature change can be converted into a visually perceivable image through the use of a non-invasive means for dynamically measuring blood flow characteristics. As noted above, an infra-red sensing device can be utilized as a non-invasive means for dynamically estimating blood flow characteristics. In particular, an infra-red system produced by AGEMA Infra Red Systems (the AGEMA 870) can be customized to work well as a means for dynamically estimating blood flow characteristics. The AGEMA 870 has heretofore typically not been used for this purpose; however, the apparatus can be adapted by techniques known to those skilled in the art to perform the desired function of estimating perfusion fields of blood vessels, and thus can be adapted for use in the methods of the present invention. This optionally involves the use of a reflecting infra-red mirror, a zoom lens with a focusing device, an adaptor and a video recorder, a keyboard for entering identifying information, a computer with image enhancement capability, a stand for the mirror, a rolling cabinet for the other equipment, a power source suitable for the operating room, two color monitors and a means for changing the angle of the mirror remotely.

The perfusate is maintained at the patient's normal mean arterial blood pressure, and the perfusion field delineation is essentially complete within about thirty seconds after infusion. Areas of the heart that do not show significant temperature change, as depicted by the means for dynamically estimating blood flow characteristics, are inadequately perfused and may require grafting.

Individual coronary arteries can also be perfused by infusing cold or warm solution into the proximal end of a graft to that artery. If the artery's perfusion field includes a nearby coronary artery, and the flow is high enough, no additional graft may be required to that nearby artery.

The methods of the present invention are as sensitive as arteriography, but have the advantage of demonstrating changes in the heart and related areas in a dynamic, blood-flow dependent fashion rather than relying solely on structural factors that show arterial narrowing which may or may not be functionally significant, for instance, in the case of multiple stenoses in one artery. Additionally, the methods of the present invention give more precise relative information from which the surgeon can make grafting decisions at the operating table rather than relying upon the feel and size of the artery.

Figures 11, 12:
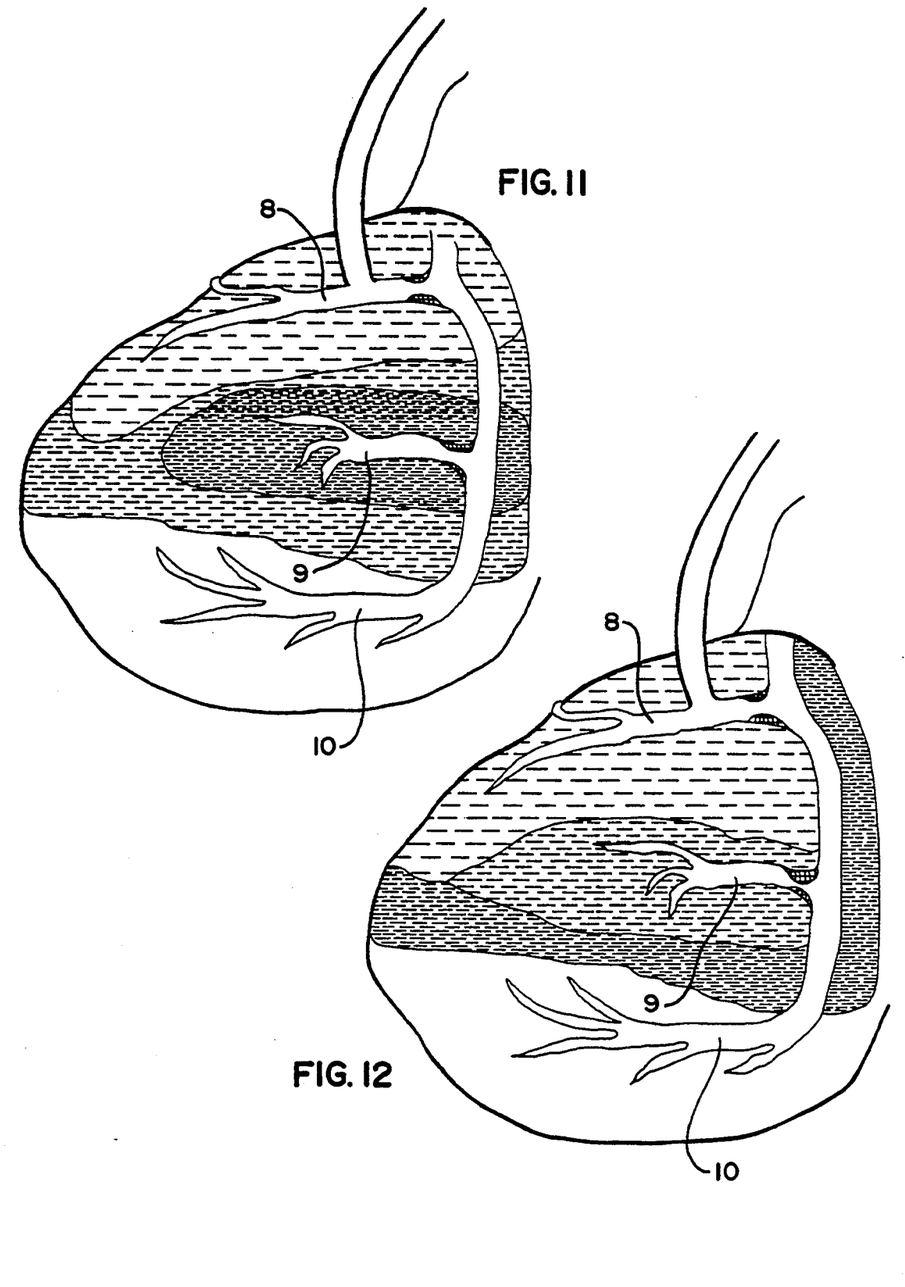
FIG. 11 is a rear elevational view of the heart in which a graft has been placed to an artery in the back of the heart evidencing moderately severe obstructions of two arteries with cooling only of the perfusion field of the artery having the graft.
FIG. 12 is a rear elevational view of the heart of FIG. 11 in which a graft has been placed to the same artery as previously, but now evidencing cooling of the perfusion fields of both arteries due to good collateral vessels between the arteries, thus defining a shared perfusion field.

For example, if a patient with a recent infarction, or advanced age or with diabetes mellitus, has occlusions of branch arteries so that an area of the heart is not adequately perfused after a graft has been placed to the regional artery, then another graft will have to be placed into a nearby artery, even if such a nearby artery has only a minor obstruction or seems to be a small and insignificant vessel on arteriography and would, therefore, normally not be chosen as a graft recipient. Conversely, if a patient has adjacent arteries that are both significantly obstructed, and a graft to one of these arteries has been placed, one can then flow cold solution through this graft and see the perfusion field of this artery (FIG. 11). In some instances, the artery's perfusion field will overlap the second artery (FIG. 12). Should the temperature change spike over the second artery, and should the blood flow through the first graft be high, then a second graft, into the second artery, will likely not be necessary. This situation is seen not infrequently at the operating table, and is clinically recognized after the second artery is opened and the perfusate from the first artery floods the operative area. In fact, placing an unnecessary graft could endanger the survival of both grafts since long term patency depends in part upon the volume of flow, and placing competitive grafts decreases the flow in each graft. This situation until now has not been discoverable before opening the second coronary artery, at which point one is essentially committed to placing the second graft.

In particular, one preferred method of the present invention of performing heart surgery comprises an assessment of the regional distribution of blood flow during open-heart surgery, both before and after coronary artery bypass grafting, as follows. Heparinizataion, arterial and venous cannulation, and institution of cardio-pulmonary bypass are accomplished in the usual fashion as are well-known in the art, as well as core-cooling if desired. Saline slush instillation into the pericardial sac for external cardial hypothermia is optional. When electrocardiographic changes occur on the EKG monitor, the ascending aorta can be distally clamped and cold cardioplegia solution (at about four degrees Centigrade) infused via a needle catheter into the proximal aorta. As a result of either cold cardioplegia infusion, or of core-cooling, or both, a temperature differential is produced between the cooled areas of myocardium supplied by the patient's open coronary arteries and the background of the warmer areas, which are poorly perfused areas of myocardium inadequately supplied by obstructed coronary arteries.

A means for dynamically estimating blood flow characteristics is employed to demonstrate in color or gray scale and with on-line computer enhancement the temperature profile in the vicinity by utilizing certain predetermined color ranges. For example, it has been found that in accordance with the present invention, a ten color range over a five degree Centigrade range works well, each color then representing a one-half degree Centigrade temperature change.

After the differential cooling of the heart and surrounding areas is demonstrated by the means for dynamically estimating blood flow characteristics, a suitable vessel for bypass is identified. Upon completion of the coronary-graft anastamosis, the graft is then infused with cold cardioplegia solution. Still using the means for dynamically estimating blood flow characteristics, the previously poorly supplied area of myocardium can be re-evaluated. A monitor displays the previous thermographic appearance of the poorly supplied, warmer area while the now well-supplied and cooler area is displayed on a second, on-line monitor. By comparing images on the two monitors, the surgeon can detect changing blood flow patterns. The surgeon is then in a position to make informed decisions about the need for additional bypasses, the choice of arteries for bypasses in that area, as well as the possible deleterious efects of further bypasses in the same area. The same steps are repeated until all areas of the heart have been so evaluated, and the operation is then completed in the usual fashion.

The methods of the present invention are further illustrated with reference to the following examples.

EXAMPLE 1

Figure 1A:
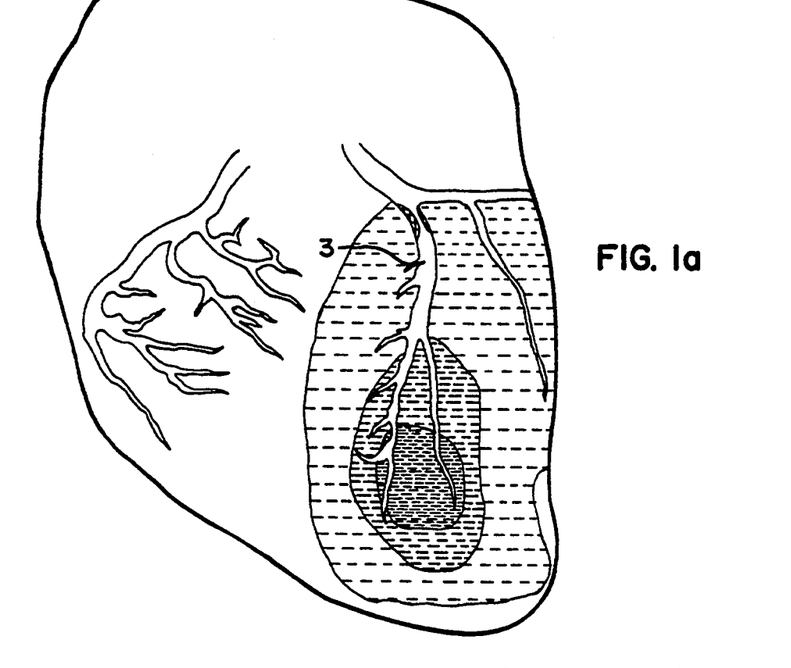
FIGS. 1a and 1b are front elevational views showing the heart and surrounding areas which are involved in coronary bypass surgery in which, in FIG. 1a, one artery exhibits moderately severe obstruction and has a warm area due to poor perfusion of cold solution. The graft to the artery shown in FIG. 1b beyond the obstruction cools the previously warm area due to good perfusion of cold solution from the graft.
Figure 1B:
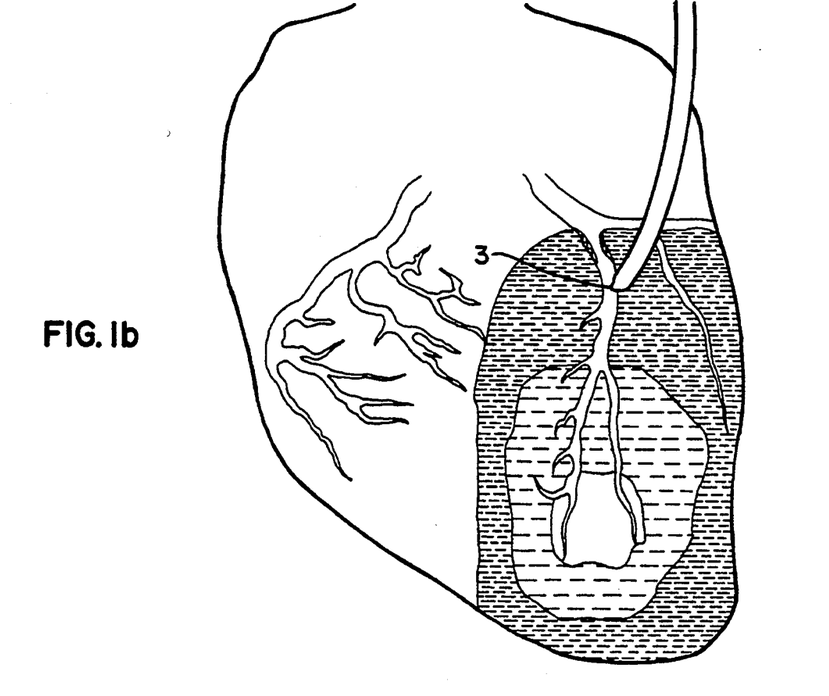

This example concerns artery 3 in FIGS. 1a and 1b. As seen in these figures, there is an obstruction in the proximal portion of the artery. The cold solution has been infused through the root of the aorta and flows into the coronary arteries. Due to the obstruction in artery 3, less cold solution reaches the artery's perfusion field, which, therefore, remains warmer. This is evidenced by the means for dynamically estimating blood flow characteristics utilizing a ten-color scale or a gray scale. A graft is then anastomosed to the artery 3 beyond the obstruction, and, when it is infused with cold solution, the previously warm area then becomes cold, again shown thermographically by a ten color scale or in gray scale. The surgeon then has dynamic proof at the operating table that the graft is functioning as it was intended to, by perfusing an area previously inadequately perfused.

If it is assumed that the obstruction in artery 3 is less severe, for instance, only 25 percent, but a long lesion instead of a discrete one, the decision whether to graft such an artery or leave it alone becomes one of the surgeon's judgment, based upon the arteriographic findings, the specific artery which is involved, the condition of neighboring arteries, the number of other arteries to be grafted, the patient's condition, the condition of the ventricle, etc. However, thermographically, the surgeon will have solid data upon which to base his or her decision. If the area perfused from the artery in question is adequately cooled by the solution infused into the aortic root, then there is no urgent need to graft the vessel. Conversely, if the perfusion bed remains warm, then there is an obvious need to bring more blood flow into the area by placing a graft.

EXAMPLE 2

Figure 2:
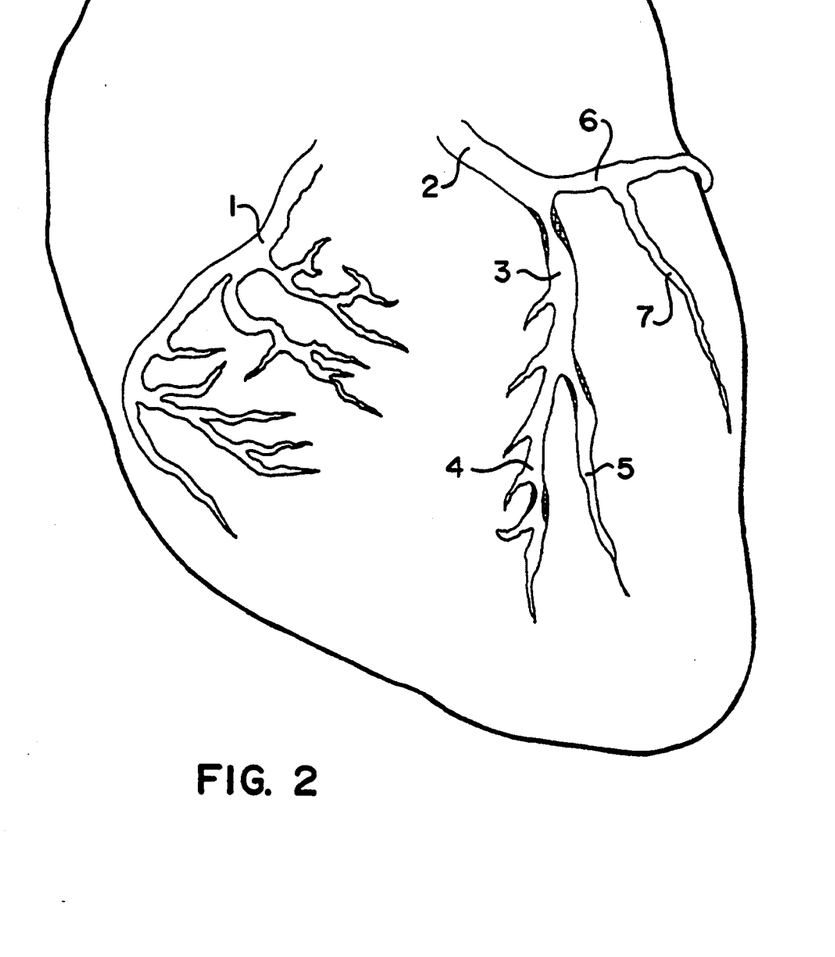
FIG. 2 is a front elevational view of the heart and various arteries in which three moderately severe obstructions are present, one in the proximal artery, one in a major branch, and one in the distal artery beyond the origin of the major branch.
Figures 3, 4, 5, 6, 7:
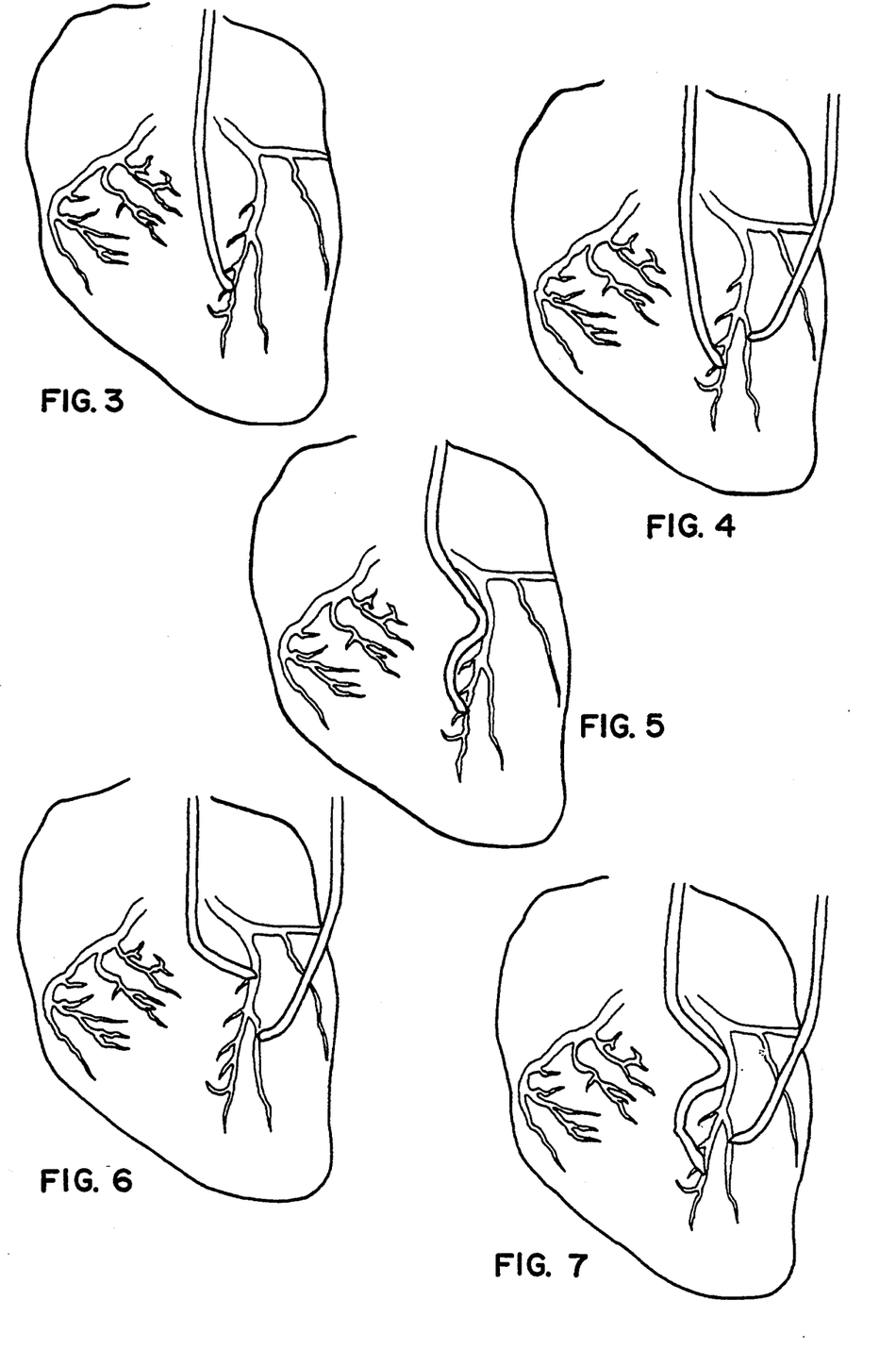
FIG. 3 is a front elevational view of the heart of FIG. 2 in which one artery has a graft beyond its obstruction.
FIG. 4 is a front elevational view of the heart of FIG. 2 in which two arteries have grafts beyond their obstructions.
FIG. 5 is a front elevational view of the heart of FIG. 2 in which one artery has a graft and a jump to another artery.
FIG. 6 is a front elevational view of the heart of FIG. 2 in which two arteries have grafts beyond their obstructions.
FIG. 7 is a front elevational view of the heart of FIG. 2 in which one artery has a graft and a jump to another artery and a graft to a third artery.

With reference to FIG. 2, there is a 50-75 percent narrowing of artery 3 as well as a 50-75 percent obstruction of artery 4 and a 75 percent obstruction of artery 5. A number of different treatment possibilties exist:
a) A graft to artery 4 only (FIG. 3);
b) Grafts to both arteries 4 and 5 (FIG. 4);
c) A jump graft to arteries 3 and 4 (FIG. 5);
d) Grafts to both arteries 3 and 5 (FIG. 6); and
e) A jump graft to arteries 3 and 4 and a graft to artery 5 (FIG. 7).

Again, the choice of the various main possibilities is one of the surgeon's judgment. By utilizinig a means for dynamically estimating blood flow characteristics, as described above, further information can be obtained which will strongly influence the decision-making process.

There are two main possibilities. First, the area of inadequate perfusion is limited to the area below the origin of arteries 4 and 5. Second, the area of inadequate perfusion is the entire perfusion field of arteries 3, 4 and 5.

Figure 8A:
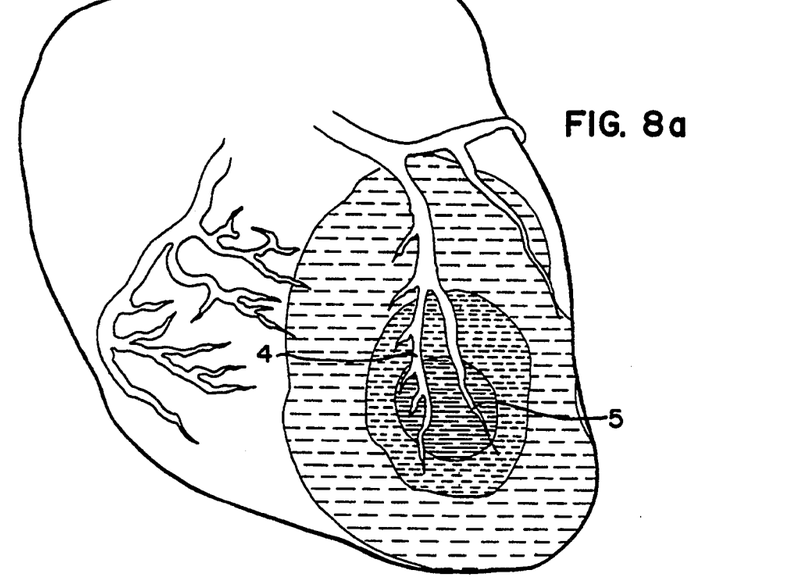
FIG. 8a is a front elevational view of the heart of FIG. 2 in which a warm area is present due to poor perfusion involving the shared perfusion fields of two arteries.
Figure 8B:
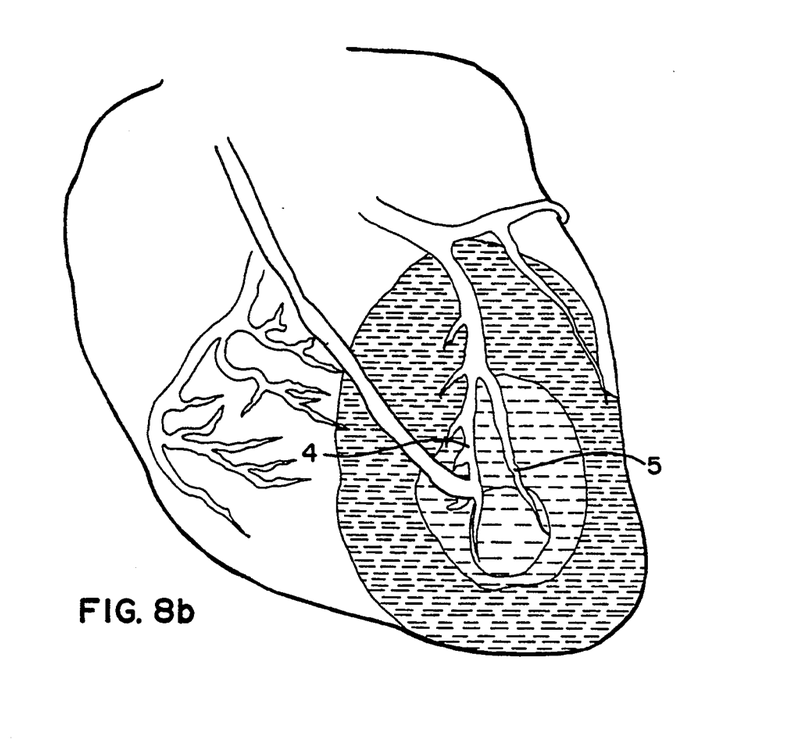
FIG. 8b is a front elevational view of the heart of FIG. 8a in which a graft has been placed to one artery beyond its obstruction, thereby creating a cooling of the previously warm area of FIG. 8a in the shared perfusion fields of the two arteries.
Figure 9A:
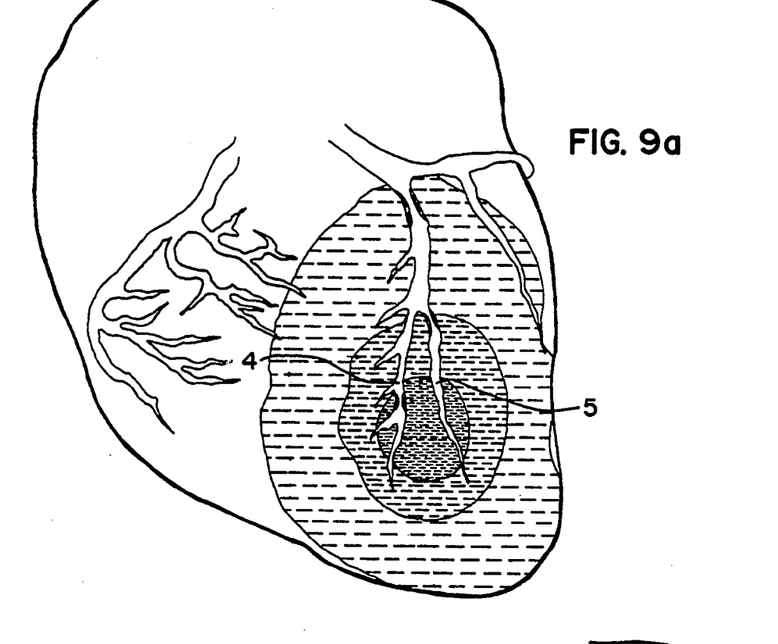
FIGS. 9a and 9b are front elevational views of the heart of FIG. 2 in which a graft to one artery is unable to cool the entire previously warm area due to a lack of collateral vessels between the two arteries.
Figure 9B:
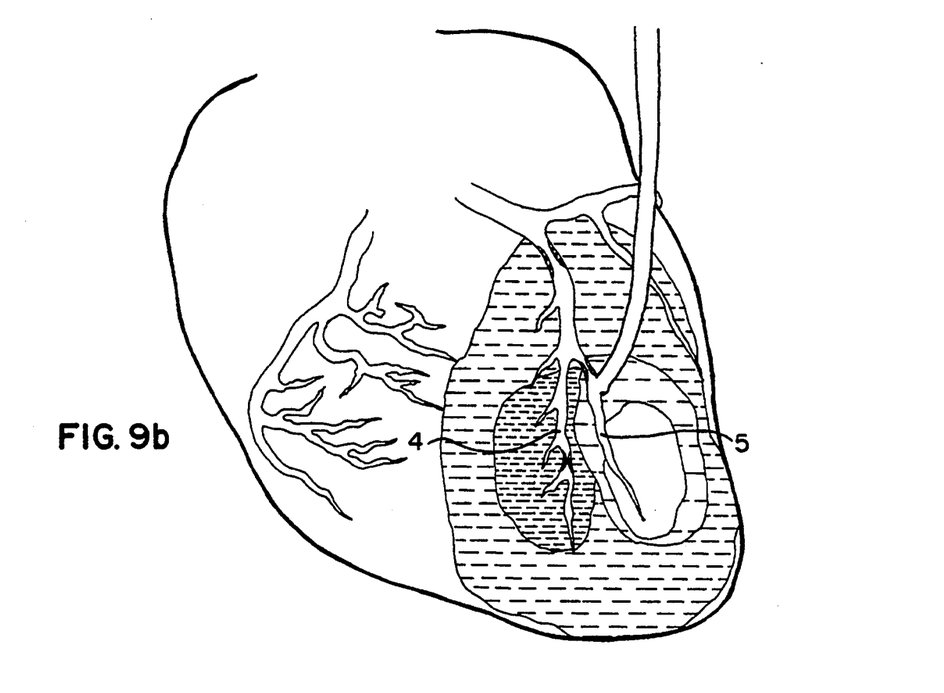
Figure 10:
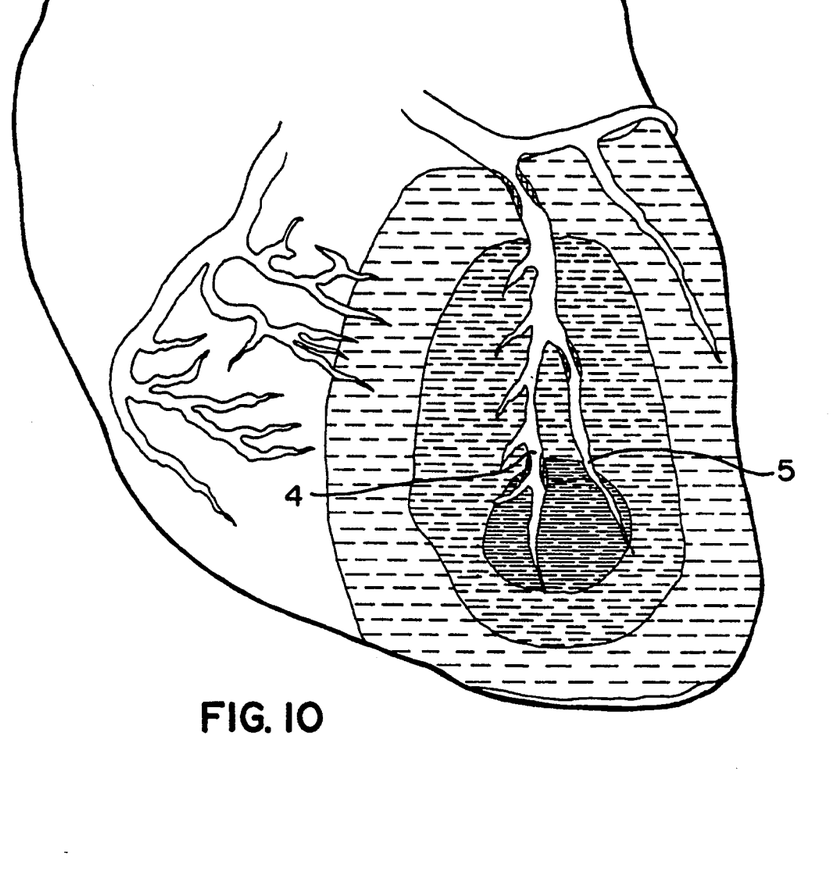
FIG. 10 is a front elevational view of the heart of FIG. 2 illustrating a warm area of inadequate perfusion in the fields of all three arteries.

In the first instance, as shown in FIGS. 8a and 8b, there will very probably be no need to place a graft into artery 3. A graft is, therefore, placed into artery 4 and the graft perfused with cold solution. If the area previously warm now becomes cold, no additional graft will likely be needed. However, if artery 4 is judged to be too hard or too small to be a good graft recipient, a graft is placed into artery 5. By the method of the present invention explained above, it is possible to know whether sufficient collateral vessels exist to obviate the need to attempt to graft into the poor quality artery 4 as well. Conversely, if the graft to artery 5 does not adequately revascularize the previously inadequately perfused area (FIG. 9), then the surgeon has a dynamic estimation of blood flow characteristics upon which to base a decision to graft artery 4 even though it appears to be of poor quality (FIG. 7).

If it is assumed that the other possibility exists, that the inadequately perfused area comprises the entire perfusion bed of arteries 3, 4 and 5 (FIG. 10), since the distal coronary artery obstruction is only 50-75 percent, it is theoretically possible that this obstruction will transmit enough blood in a retrograde fashion so that a graft to artery 4 will also supply artery 3. A graft is, therefore, placed to artery 4 (FIG. 3) and the method of Example 1 is repeated to see if the perfusion field of artery 3 is adequately supplied with flow. If it is not, then the graft is converted into a jump graft as in FIG. 5.

Conversely, if artery 4 is felt to be a poor quality vessel, a graft can first be placed into artery 3. If the flow to the perfusion bed of artery 4 is good, then this poor quality artery will not necessarily need to be opened. If the flow is not enough, as seen thermographically, and artery 5 seems to be a significantly better vessel, a graft is then inserted into artery 5 (FIG. 6) and the method of Example 1 is repeated. If the flow to the previously inadequately perfused area now is acceptable, the surgeon is left with the treatment possiblity as shown in FIG. 6. If the flow still is not good enough, then the surgeon has a valid reason, based on dynamic blood flow characteristics, for placing a third graft into artery 4 despite the increased risk (FIG. 7).

In the above examples, the grafts discussed have been primarily discontinuous grafts, whose distal ends are anastomosed to a coronary artery and whose proximal ends are available for infusion with cold solution. Subsequently, the proximal ends of the grafts are anastomosed to a source of arterial blood flow with a good head of pressure, usually the proximal aorta.

It is occasionally preferable to anastomose the proximal end of a discontinuous graft to the proximal aorta prior to anastomosing the distal end to a coronary artery. The steps of Example 1 can be followed with one modification, that is, cold solution is infused into the graft by infusing it into the aortic root instead of directly into the graft. The cold solution will, of course, flow also into the native coronary arteries as well as into any previously anastomosed grafts, but this will cause no confusion as inadequately perfused areas will still remain warmer, and adequately perfused areas will all attain essentially the same coolness.

Sometimes, continuous grafts are used, usually arteries proximally attached to their anatomic origins, such as the internal mammary artery or the gastroepiploic artery. In order to define the perfusion field of a coronary artery to which such a graft is anastomosed, one must temporarily remove the atraumatic clamp from the graft which keeps the graft from bleeding into the field. Once the clamp is removed, the body-temperature blood is permitted to flow through the graft and into the coronary artery and its perfusion field. Usually the body temperature is more than five degrees warmer than even the inadequately perfused "warm" areas of the heart, and a good reading can be obtained. If the body-temperature is less than five degrees warmer, the heart can be quickly cooled externally with the instillation of cold slush into the pericardial sac before releasing the atraumatic clamp and then following the method of Example 1, except that the area of the perfusion bed will be defined by warming rather than by cooling.

Although the above examples concern applications of the present invention for heart surgery, it will be readily apparent to those skilled in the art that the methods of the present invention are also applicable to surgery on other organs and areas of the body, such as the liver, kidneys, spleen, etc.

The foregoing is intended as illustrative of the present invention but not limiting. Numerous variations and modifications may be effected without departing from the true spirit and scope of the invention.

What is claimed is:

1. A method of performing heart surgery comprising the steps of:
   (a) preparing a patient for coronary bypass surgery, said patient having a heart including heart tissue;
   (b) assessing blood flow characteristics in said heart tissue;
   (c) making decisions on graft location and the number of grafts based substantially upon step (b) and placing or not placing a graft or grafts in accordance with said decisions; and
   (d) completing said surgery.

2. The method of claim 1 wherein the step of assessing blood flow characteristics in said heart tissue comprises employing a means for estimating volumetric blood flow and distribution of blood flow.

3. The method for performing heart surgery of claim 1 wherein said blood flow assessment of step (b) is done dynamically.

4. The method of performing heart surgery of claim 1 wherein said blood flow assessment of step (b) is accomplished by assessing the temperature of at least a portion of said heart tissue.

5. The method of performing heart surgery of claim 4 wherein said temperature assessment is accomplished thermographically.

6. The method of performing heart surgery of claim 1 wherein said decisions on graft location and the number of grafts is based solely upon step (b).

7. (four times amended) A method of performing bypass surgery on a coronary artery of a patient wherein one or more bypass grafts are attached to said coronary artery at selected locations, said method comprising the steps of:
   (a) preparing said patient for surgery, said patient having a heart, including heart tissue, said coronary artery attached to at least a portion of said heart tissue;
   (b) assessing temperature characteristics of said heart tissue;
   (c) making decisions on bypass graft location and number based substantially upon said temperature assessment of step (b) and placing or not placing a graft or grafts in accordance with said decisions, and
   (d) completing said surgery.

8. The method for performing heart surgery of claim 7 wherein said temperature assessment of step (b) is done dynamically.

9. The method of performing heart surgery of claim 8 wherein said temperature assessment is accomplished thermographically.

10. The method of performing heart surgery of claim 7 wherein said decisions on graft location and number of grafts is based solely upon said temperature assessment of step (b).

11. A method for performing heart surgery on a patient having a heart, including heart tissue, and a coronary artery attached to said heart, said method comprising, in the following order, the steps of:
    (a) preparing a patient for surgery;
    (b) assessing blood flow characteristics in said heart tissue of said patient; and
    (c) attaching a bypass graft at a selected position along said coronary artery, said selected position chosen based substantially on the blood flow assessment of step (b).

12. The method of performing heart surgery of claim 11 further comprising the following step:
    (d) assessing blood flow characteristics in said heart tissue of said patient after attaching said bypass graft.

13. The method for performing heart surgery of claim 11 wherein said selected position is chosen based solely on the blood flow assessment of step (b).

14. A method of performing surgery to bypass one or more portions of an artery, said artery normally supplying blood to heart tissue, said method comprising the following steps:
    (a) identifying one or more locations of stenosis within said artery;
    (b) performing a first dynamic assessment of blood flow characteristics of said heart tissue to which blood is normally supplied by said artery, said dynamic assessment including use of thermographic imaging; and
    (c) placing a first graft in said artery at a first point located downstream from one of said one or more locations of stenosis, based substantially on information obtained from step (b).

15. The method of claim 14 further comprising the following steps:
    (d) performing a second dynamic assessment of blood flow characteristics of said heart tissue to which blood is normally supplied by said artery, said dynamic assessment including use of thermographic imaging; and
    (e) placing a second graft into said artery at a second point selected based at least in apart upon information obtained from the assessment of step (d).

16. The method of claim 15 wherein a single blood-carrying vessel is used for said first graft and said second graft.

17. The method of claim 15 further comprising the following step:
(f) performing a third dynamic assessment of blood flow characteristics of that portion of said heart tissue to which blood is normally supplied by said artery, said dynamic assessment including use of thermographic imaging.

18. The method of claim 17 further comprising the following step:
(g) comparing the third dynamic assessment of step (f) with the second dynamic assessment of step (d).

19. The method of claim 15 wherein:
said artery includes a first branch and a second branch;
said first point is located in said first branch; and
said second point is located in said second branch.

20. The method of claim 17 wherein step (f) includes employing a means for estimating volumetric blood flow and distribution of blood flow to said heart tissue.

21. The method of claim 14 further comprising the following steps:
(d) performing a second dynamic assessment of blood flow characteristics of said heart tissue to which blood is normally supplied by said artery, said dynamic assessment including use of thermographic imaging; and
(e) placing a second graft into said artery at a second point upstream from said first point when said assessment of step (d) reveals an ischemic area of said heart tissue located upstream from said first point.

22. The method of claim 21 wherein a single blood-carrying vessel is used for said first graft and said second graft.

23. The method of claim 14 wherein step (b) includes the following steps:
determining a temperature for said heart;
perfusing said artery with a perfusing solution that is at least 5 degrees Centigrade lower than said heart tissue temperature;
sensing infra-red radiation emanating from said heart tissue.

24. The method of claim 14 wherein step (a) includes the following steps:
perfusing said artery with a perfusing solution having a temperature which creates a temperature differential between said perfusing solution and said heart tissue;
sensing infra-red radiation emanating from said heart tissue.

25. The method of claim 14 wherein step (b) includes employing a means for estimating volumetric blood flow and distribution of blood flow to said heart tissue.

26. The method of performing surgery of claim 14 wherein said first graft is placed at said first point based solely on information obtained from step (b).

* * * * *